United States Patent
Lourenco et al.

(10) Patent No.: US 7,094,224 B2
(45) Date of Patent: Aug. 22, 2006

(54) DEVICE FOR INJECTING A DOSE OF LIQUID IN PARTICULAR MEDICINAL LIQUID

(75) Inventors: Armindo Lourenco, Noyelles-Godault (FR); Benoît Steimer, Strasbourg (FR)

(73) Assignee: Glaxo Group Limited, Greenford (GB)

( * ) Notice: Subject to any disclaimer, the term of this patent is extended or adjusted under 35 U.S.C. 154(b) by 44 days.

(21) Appl. No.: 10/169,510

(22) PCT Filed: Jan. 5, 2001

(86) PCT No.: PCT/FR01/00031

§ 371 (c)(1),
(2), (4) Date: Sep. 11, 2003

(87) PCT Pub. No.: WO01/49347

PCT Pub. Date: Jul. 12, 2001

(65) Prior Publication Data

US 2004/0116874 A1    Jun. 17, 2004

(30) Foreign Application Priority Data

Jan. 7, 2000  (FR) .................................. 00 00192
Jan. 7, 2000  (FR) .................................. 00 00193

(51) Int. Cl.
*A61M 5/315*  (2006.01)

(52) U.S. Cl. .................................................. 604/227
(58) Field of Classification Search ................ 604/110, 604/187, 188, 189, 190, 191, 192, 193, 194, 604/195, 196, 197–199, 227
See application file for complete search history.

(56) References Cited

U.S. PATENT DOCUMENTS

| 4,929,232 | A |   | 5/1990  | Sweeney et al.          |
|-----------|---|---|---------|-------------------------|
| 4,973,318 | A |   | 11/1990 | Holm et al.             |
| 5,519,931 | A | * | 5/1996  | Reich .......... 29/426.3 |
| 5,582,595 | A | * | 12/1996 | Haber et al. ...... 604/187 |
| 5,828,073 | A | * | 10/1998 | Zhu et al. ........ 250/506.1 |
| 5,833,668 | A | * | 11/1998 | Aguilar ........... 604/227 |
| 6,132,400 | A | * | 10/2000 | Waldenburg ...... 604/191 |
| 6,186,980 | B1 |  | 2/2001  | Brunel ............ 604/110 |
| 6,576,918 | B1 | * | 6/2003  | Fu et al. ......... 250/507.1 |
| 6,585,702 | B1 |  | 7/2003  | Brunel ............ 604/263 |
| 6,626,864 | B1 | * | 9/2003  | Jansen et al. ...... 604/110 |

FOREIGN PATENT DOCUMENTS

| DE | 295 15 752 | 1/1996  |
| DE | 91 17 140  | 8/1996  |
| EP | 0 471 335  | 2/1992  |
| FR | 2390966    | 12/1978 |

(Continued)

Primary Examiner—Manuel Mendez
(74) Attorney, Agent, or Firm—Kathryn L. Sieburth; Mary E. McCarthy; Charles M. Kinzig (57) ABSTRACT

An injection device includes a syringe body tubular element (9) provided with finger-pressing members (23) for holding the injection device to inject a dose of liquid, in particular medicinal liquid. The finger-pressing members consist of a flange (23), provided with an upper surface and a lower surface, including two portions with symmetrical outline (50, 51), called gripping portions, having lower support surfaces for the user's fingers, and between the support surfaces, two portions with diametrically opposed symmetrical outlines (52), called indexing portions, including in the extension of the lower surface of the flange, a lower surfaces having a convex profile formed by two slopes symmetrical relative to a longitudinal axis.

8 Claims, 8 Drawing Sheets

FOREIGN PATENT DOCUMENTS

| | | | | | |
|---|---|---|---|---|---|
| FR | 2784033 | 4/2000 | WO | WO 99/17823 | 4/1999 |

\* cited by examiner

180
DEVICE FOR INJECTING A DOSE OF LIQUID IN PARTICULAR MEDICINAL LIQUID

The invention concerns a device for injecting a dose of liquid, in particular a medicinal liquid.

At the present time, for purposes of hygiene and security, most injection devices are single-use devices and comprise, besides a conventional or unconventional syringe, protective elements designed to shield the needle after use and to prevent any subsequent re-use of the injection device.

Such injection devices thus consist of a plurality of elements including an element provided with finger rest components which are generally led between two parallel rails and distributed to assembly machines designed for securing them in translation.

In addition, as a general rule, the various elements of injection devices are provided with means for stopping in rotation, enabling them to be locked in rotation with respect to each other. To this end, assembly lines are thus provided with specific means for locating the angular position of the elements and in particular of the element provided with finger rest components and for indexing this angular position with a view to enabling assembly to take place.

In addition, once the assembly has taken place, and in order to guarantee the prior non-use of injection devices, two solutions currently exist.

The first solution consists of packaging these injection devices in a sterile package of the pocket or blister type etc.

The second solution consists of fitting these injection devices with a detachable protective cap capable of covering the rear portion of the element provided with finger rests, so as to be butted up against said finger rest components. According to this solution, moreover, the protective cap and the conventional needle-protecting end piece are secured by security seals, such as spot welds, aimed at making it possible to verify and to guarantee that any one of these two elements has not been previously removed.

The value of this second solution lies in the fact that "inviolability" of the product is obtained by means of a simple protective cap which, on the one hand, may be put in place directly on the assembly line without requiring any subsequent packaging operation and which, on the other hand, restricts the overall size of the finished products compared with those obtained according to the first solution.

The major disadvantage of this second solution lies on the other hand, in the fact that "inviolability" requires the protective cap to be secured which in practice makes it necessary to exert a relatively high force with a view to removing this protective cap.

The present invention aims in the first instance to simplify assembly lines and has a first objective of providing an injection device of which the indexing in rotation of the element provided with finger rest components is obtained in an automatic manner without the need for specific means.

Another objective of the invention is to provide an injection device of which the operation of assembling the element provided with finger rest components with another element is obtained in a very simple manner.

Another objective of the invention is to provide an injection device comprising a protective cap ensuring the "inviolability" of said injection device and which can be removed very easily.

To this end, the invention first of all concerns an injection device comprising a syringe body tubular element provided with finger rest components designed for gripping said injection device with a view to injecting a dose of liquid, in particular a medicinal liquid, said injection device being characterised in that the finger rest components consist of a collar, provided with an upper surface and a lower surface, including two portions with a symmetrical outline, called gripping portions, having lower supporting surfaces for the user's fingers, and between said supporting surfaces, two portions with diametrically opposed symmetrical outlines, called indexing portions, including in the extension of the lower surface of said collar, a lower surface having a convex profile formed by two slopes symmetrical with respect to a longitudinal axis.

The specific shape of the finger rest collar of the injection device according to the invention advantageously leads, when the element provided with this collar is conveyed between two parallel rails, to this element being pivoted automatically on itself until a stable angular transporting position is obtained in which the gripping portions rest on said rails.

On account of this, whatever the initial angular position in which the element provided with the collar is positioned between the rails, the final orientation obtained is always substantially the same, so that indexing of this element in rotation requires neither a locating device nor an indexing device.

It should moreover be noted that precision as regards the final orientation obtained is a function of the length of the upper base of the profiles with a convex shape. Indeed, if this upper base has a length greater than or equal to the diameter of the tubular element, the final orientation obtained is always strictly the same. On the other hand, if this length is less than this diameter, the orientation obtained may vary by a few degrees according to the difference in length.

Advantageously, each indexing portion of the collar includes a lower surface having a curved profile with a convex rounded shape.

In addition, according to an advantageous embodiment, each indexing portion of the collar has the shape of an undulation defining an indentation with a concave shape.

Such indentations make it possible in particular, as will be better understood further on, to guarantee that the indexing position of the element provided with the finger rest collar is maintained during assembly of the latter with another element on an assembly machine. Indeed, maintenance of this indexing position may be ensured in a very simple manner by using a tubular tool capable of covering the element provided with the collar, comprising an end section with a shape mating with that of the upper surface of the collar, and thus having two portions with a convex profile having a shape mating with the concave shape of the indentations. Moreover, this tubular tool leads to a correction of any errors in orientation, in the case in particular where the length of the upper base of the indentations is less than the diameter of the tubular element.

According to an advantageous embodiment, the injection device includes a protective cap capable of covering the rear section of the tubular element of the syringe body so as to become butted up against the collar.

In this case and advantageously, according to the invention, the protective cap has a peripheral wall provided with an end section comprising, for each indexing portion of the finger rest collar, a peripheral wall portion, called the assembly portion, having a curved profile with a convex rounded form complementary to the upper surface of said indexing portion, adapted so as to fit into the latter.

This protective cap and the finger rest components of the syringe body thus possess assembly portions leading in the first place to obtaining a tightening force on account of the convex and concave complementary shape of the contacting surfaces, and enabling "inviolability" to be ensured by means of an optional seal which has a low strength and thus can easily be broken.

Moreover, the protective cap can be removed by turning the latter in one or other directions of rotation, rotation during which profiles of the assembly portions of said cap and of the finger rest components cause an axial displacement of this cap, so that removal of the latter is similar to a simple unscrewing operation not requiring the exertion of any considerable force.

It is to be noted, moreover, that the presence of two symmetrical assembly portions leads, on the one hand, to an increase in the tightening force obtained, and, on the other hand, leads to the easier removal of the protective cap on account of the fact that displacement of the latter results from a force of which the resultant is perfectly axial.

Moreover, advantageously, the protective cap includes at least one internal component for locking in translation projecting with respect to the inner surface of the peripheral wall of said cap, the tubular element of the syringe body including a peripheral wall of which the external surface has, in a position mating with each of said means for locking in translation, a recess capable of housing the latter.

Such means for locking in translation make it possible to reduce to its simplest expression the strength of the security seal aimed at guaranteeing "the inviolability" of the injection device, and even of eliminating the latter.

Moreover, advantageously, the means for locking the protective cap in translation consist of two diametrically opposing inner catches, each recess of the syringe body consisting of an opening capable of housing one of said catches.

Other characteristics, objectives and advantages of the invention will become apparent from the following detailed description with reference to the accompanying drawings which represent, as a non-limiting example, a preferred embodiment. In these drawings.

Figure 1:
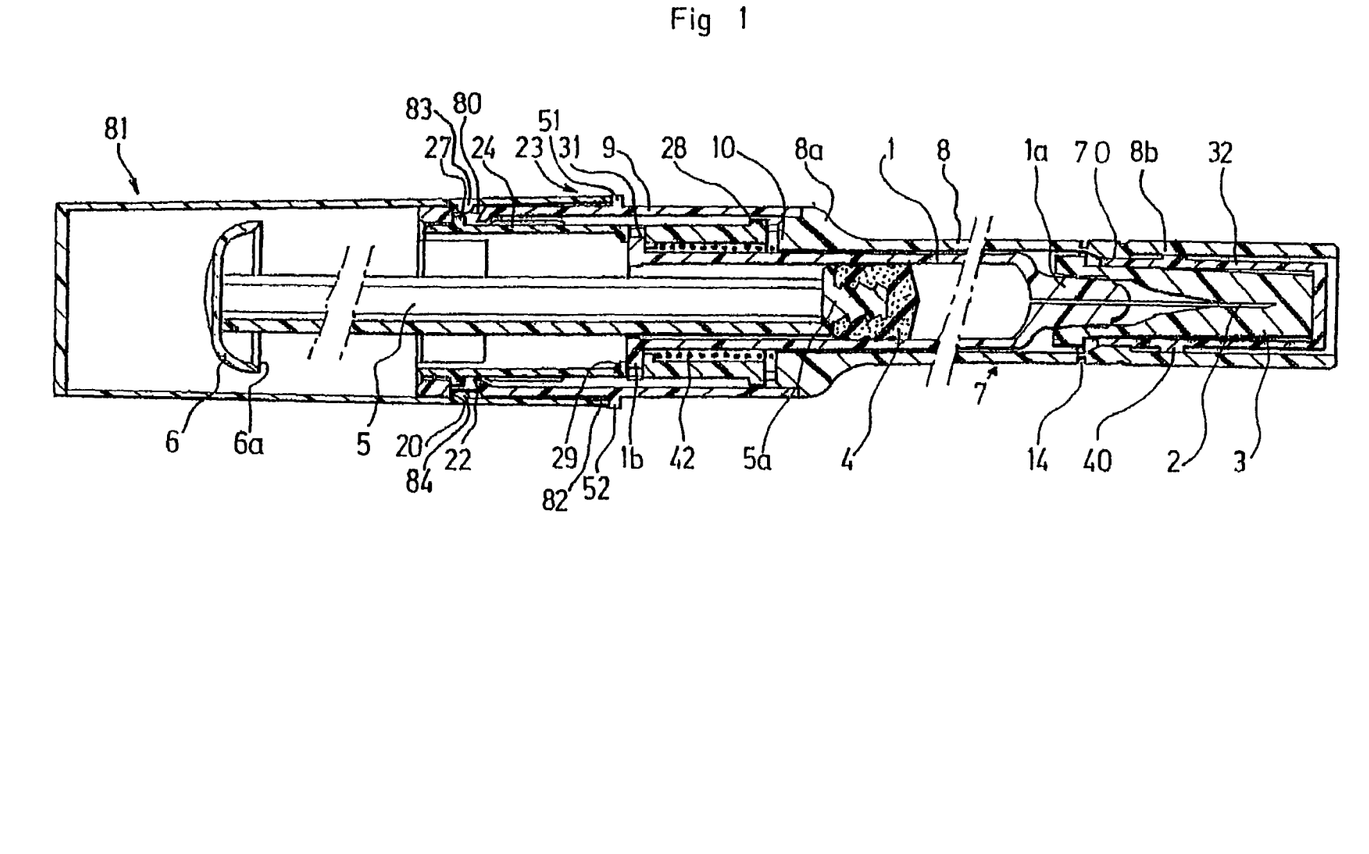
FIG. 1 is a longitudinal section through an axial plane of an injection device according to the invention shown before use.

The injection device according to the invention shown in FIG. 1 comprises, first of all, a pre-filled syringe 1 of the traditional type, such as for example one made of glass, carrying in a conventional manner a front nose 1a on which is mounted a needle 2, and a collar 1b at its rear end.

This syringe 1 also carries, in a conventional manner, an end piece 3 for protecting the needle 2 adapted so as be mounted in a leakproof manner on the front nose 1a of said syringe.

It also includes, in a conventional manner, a piston 4 delimiting the chamber filled with a dose of liquid, drilled by a tapped blind bore in which is screwed the threaded end 5a of a piston rod 5 provided at its opposite end with a thrustor 6.

This thrustor 6 is in the form of a cup having a section 6a with an oblique profile for purposes that will be explained later.

The injection device according to the invention also includes an assembly for protecting the syringe 1 adapted so as to be entirely pre-assembled before said initially pre-filled syringe is put in place in said protective assembly.

This protective assembly comprises first of all a protective case 7 shown in FIGS. 3 to 7, composed of two tubular bodies, a front one 8 and a rear one 9, adapted so as to fit in the extension of each other.

Figure 3:
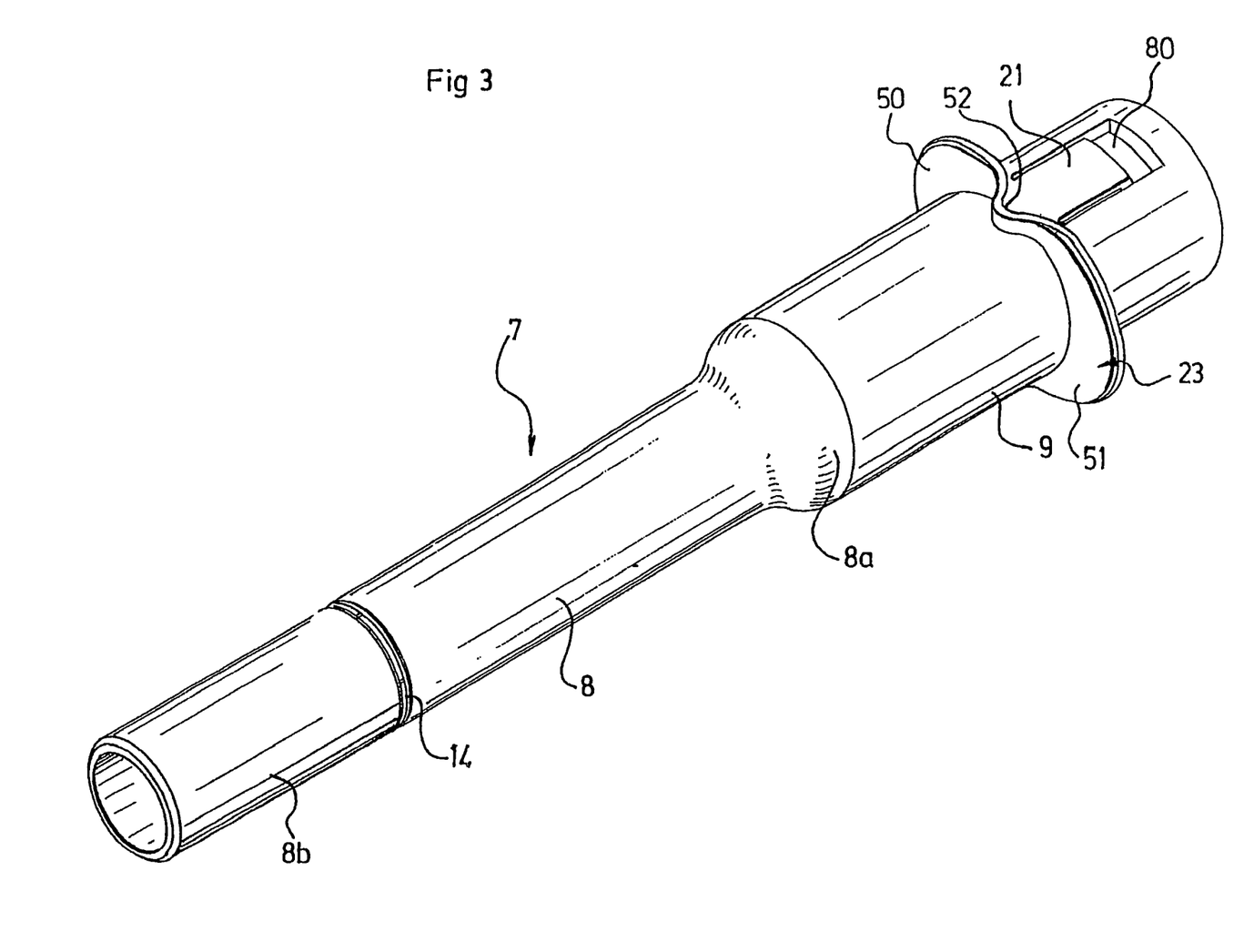
FIG. 3 is a perspective view of a first element, consisting of a protective case, of this injection device.

The front body 8 has an internal diameter mating with the external diameter of the syringe 1 and a length adapted to house the needle 2 provided with its needle-protecting end piece 3 and substantially 80% of the length of the syringe 1.

At its rear end, this front body 8 has a rear section 8a with a substantially ovoid external shape with external diameters greater than the standard external diameter of said front body, recessed internally so as to include internal longitudinal ribs such as 10 defining an internal diameter identical to that of the standard internal diameter of this front body 8.

Each of these ribs 10 has, additionally, a shoulder 10a delimiting a rear end portion having an internal diameter substantially greater than the diameter of the syringe 1.

Figure 6:
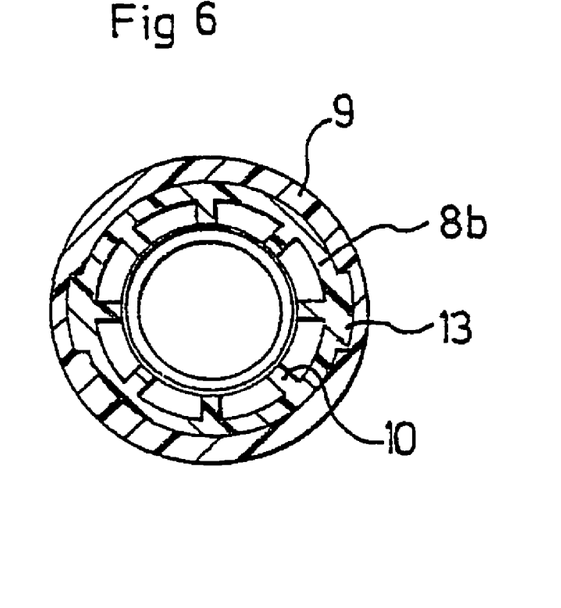
FIG. 6 is a cross section through a plane C of this protective case.
Figure 7:
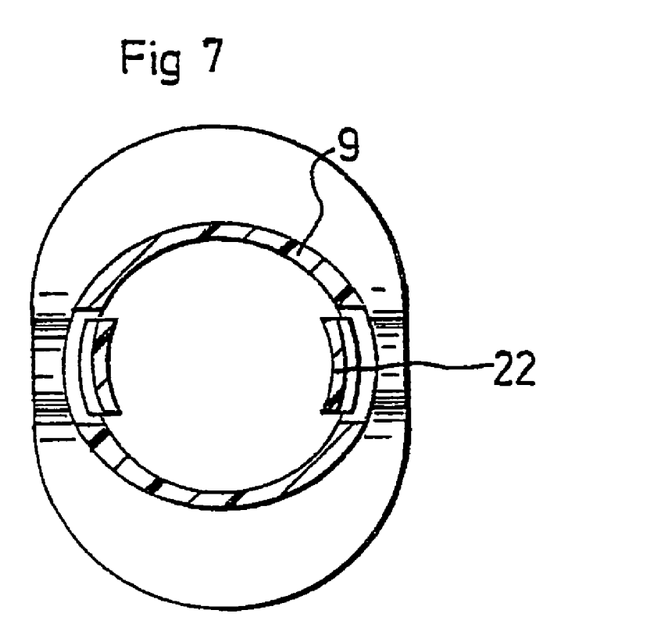
FIG. 7 is a cross section through a plane D of this protective case.

On the outside, this rear section 8a includes an annular groove 11 delimited by a rear circlip 12. In addition, as shown in FIG. 6, this groove 11 is interrupted by two diametrically opposed catches such as 13 projecting radially with respect to the circlip 12.

In the region of its front end, the front body 8 includes a cleavable front section 8b delimited by a breakable annular zone 14 positioned so as to be situated substantially in the region of the front nose 1a of the syringe 1 once this is put in place.

Figure 4:
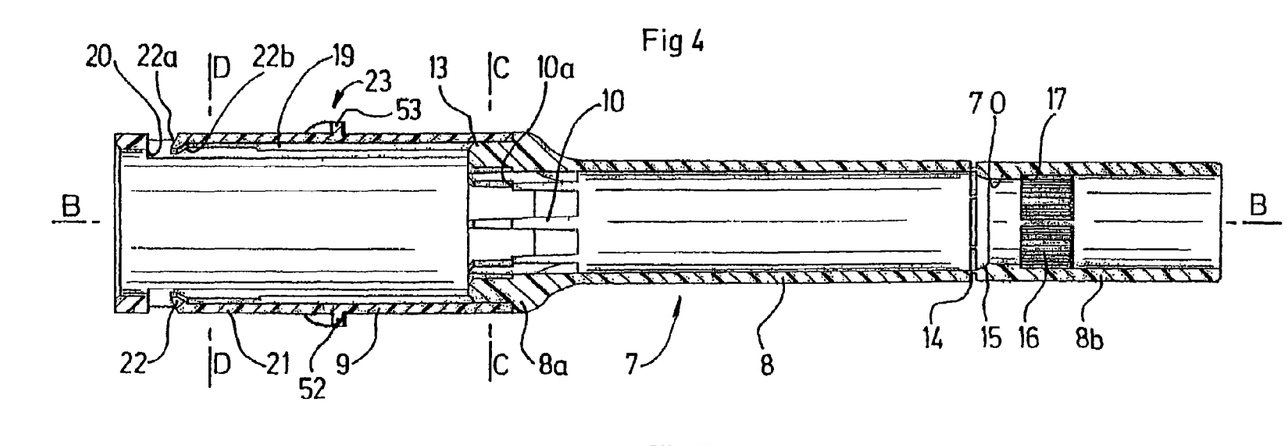
FIG. 4 is a longitudinal section through an axial plane A of this protective case.
Figure 5:
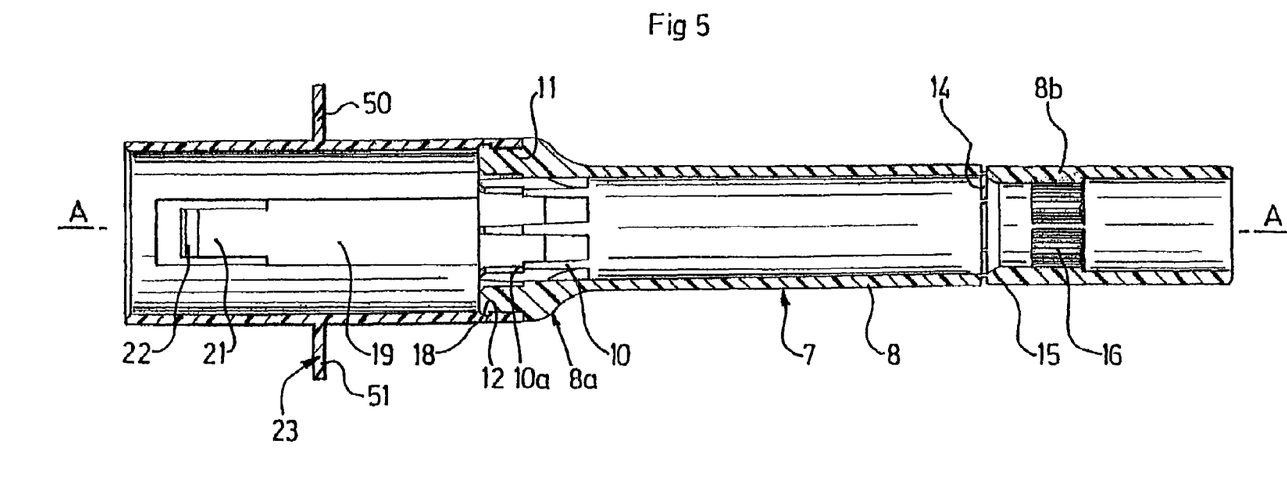
FIG. 5 is a longitudinal section through an axial plane B of this protective case.

This cleavable section 8b has, internally, in the region of its rear end, an oblique profile 15 forming an access slope with a rear portion constituting a neck 70 with a diameter substantially less than that of the standard internal diameter of front body 8.

The front of this neck 70 and the cleavable section 8b additionally include a plurality of longitudinal notches such as 16 distributed over the periphery of the internal surface of said cleavable section and delimiting an internal diameter identical to that of said neck, so that the grooves between said notches define a shoulder 17 with the front end of this neck 70.

Finally, concerning this cleavable section 8b, the front portion of the latter situated in front of the notches 16 has an internal diameter identical to the diameter separating the bottom of the notches.

As regards the rear body 9, this has a substantially ovoid shape mating with that of the rear section 8a of the front body 8, adapted so as to fit over said rear section 8a.

To this end, this rear body 9 has, first of all, an internal annular groove 18 arranged so as to house the circlip 12. It also includes two diametrically opposed internal longitudinal grooves such as 19, each capable of housing a catch 13, so as to ensure that the two bodies 8, 9 are locked in rotation, said grooves being interrupted a short distance from the rear end of this rear body 9, so that the latter has an internal shoulder 20 at the level of the end of these grooves 19.

As shown in FIG. 6, the grooves 19 are arranged along the largest diameter of the rear body 9 so as to minimise the thickness of the wall of said rear body.

The rear body 9 additionally has two deformable tongues such as 21, each arranged in a groove 19 in the region of rear end of the latter. Each of these tongues 21 is formed by a U-shaped cut-out arranged in the wall of said rear body, and an opening such as 80, in particular for demoulding, is provided in said wall, upstream from each tongue 21.

Each of these tongues 21 has, in the region of its rear end, a transverse hook 22 projecting inside the rear body 9. Each of these hooks has a substantially radial non-return rear surface 22a and an oblique front surface 22b forming a slope.

Finally, the rear body 9 has an external finger support collar 23.

According to the invention, this collar 23 with a generally annular shape comprises:
  two substantially flat diametrically opposed contoured portions 50, 51 defining two surfaces for supporting the fingers of the user, and
  between the supporting surfaces 50, 51, two diametrically opposed undulations 52, 53, defining two curved indentations with a concave shape.

Figure 8:
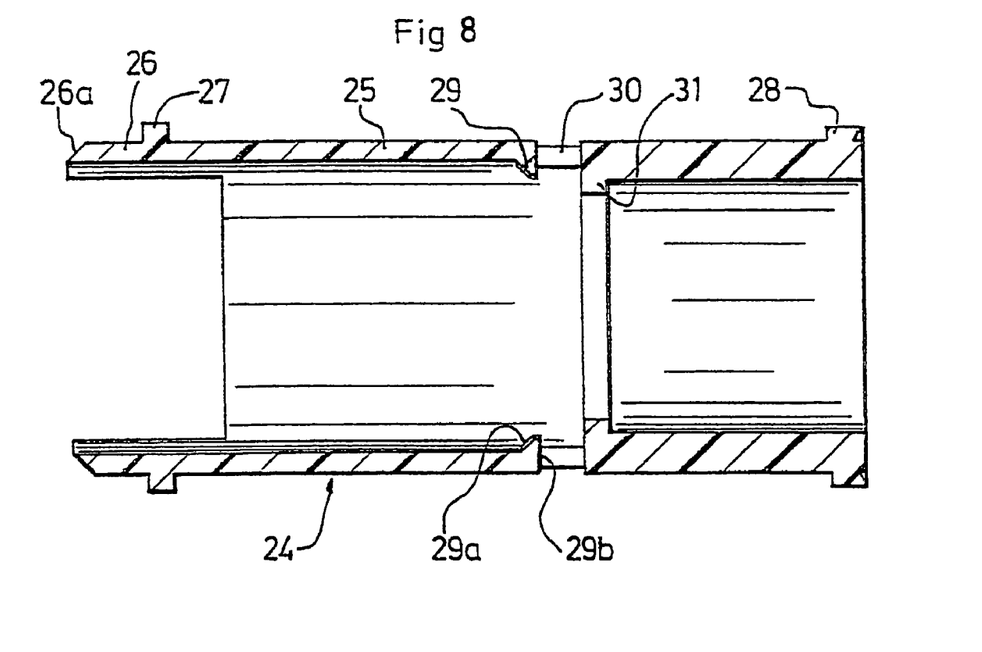
FIG. 8 is a longitudinal section through an axial plane E of a second element, consisting of a locking ring, of this injection device.
Figure 9:
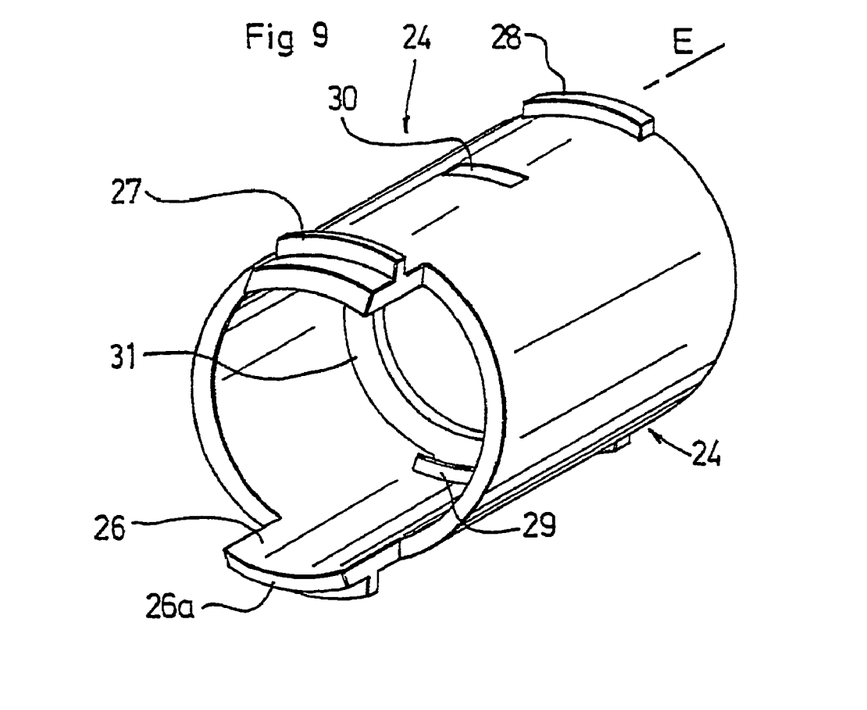
FIG. 9 is a perspective view of this locking ring.

Secondly, the protective assembly includes a locking ring 24 with a shape adapted so as to be inserted inside the rear body 9, while being presented facing the front surface of the latter.

This locking ring 24 with a length adapted so as to be inserted inside the rear body 9, is in the form of a cylindrical sleeve 25 extended to the rear by two diametrically opposed lugs such as 26 in the form of a cylindrical sector.

Each of these two lugs 26 has, first of all, a rear end surface 26a with an oblique profile complementary to that of the section 6a of the thrustor 6 of the piston rod 5.

Each of these lugs 26 additionally has, substantially at mid-length, a transverse external rib 27, adapted so as to slide in one of the grooves 19 of the rear body 9.

The cylindrical sleeve 25 of this locking ring 24 includes, based on the same generators as the transverse ribs 27, two transverse ribs such as 28 also adapted so as to slide in the grooves 19 of the rear body 9 and provided in the region of the front end of said sleeve.

This cylindrical sleeve 25 also includes substantially at mid-length and in the axial alignment of the aforementioned ribs 27, 28 two diametrically opposed internal ribs such as 29, and downstream from each of these the peripheral wall of said sleeve is pierced by an opening such as 30 enabling the undercut to be demoulded.

Each of these internal ribs 29 has a rear surface 29a with an oblique profile forming a slope and a non-return locking radial front surface 29b.

Finally, the cylindrical sleeve 25 includes, downstream from the openings 30 and away from the internal ribs 29 mating with the thickness of the collar 1b of the syringe 1, an annular internal shoulder 31.

Figure 10:
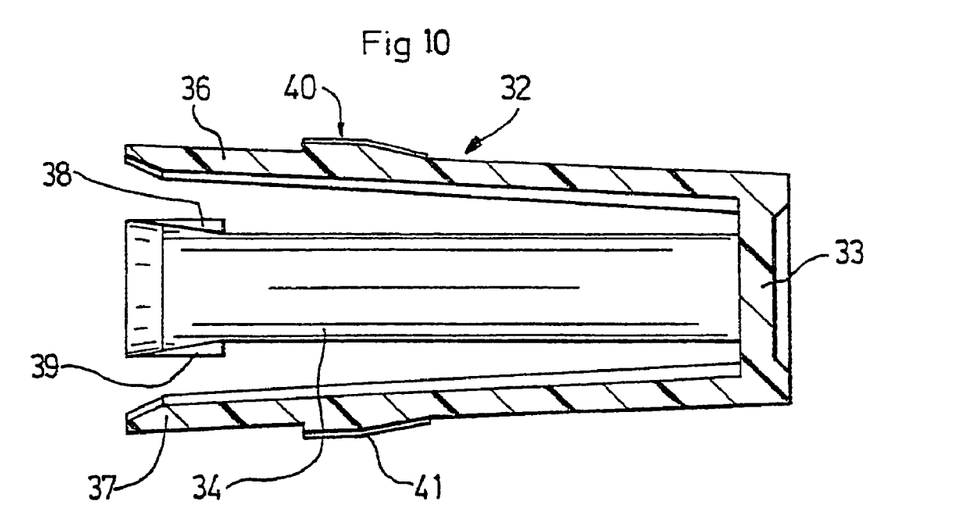
FIG. 10 is a longitudinal section through an axial plane F of a third element, consisting of an end piece with dogs of this injection device.
Figure 11:
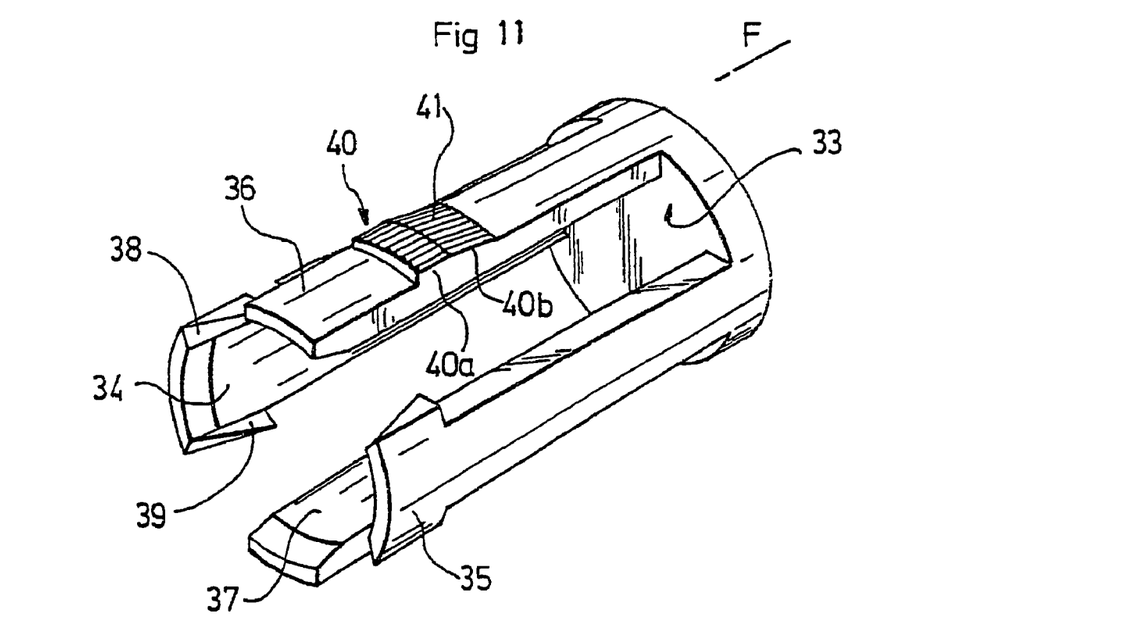
FIG. 11 is a perspective view of this end piece with dogs.

The injection device according to the invention additionally includes an end piece with dogs 32 shown in FIGS. 10 and 11, designed to cover the needle-protecting end piece 3 and to bring about withdrawal of the latter after rupture of the breakable zone 14 of the front body 8 of the protective case 7.

This end piece with dogs 32 has a cylindrical front wall 33, with a diameter adapted so as to penetrate the cleavable section 8b, in the periphery of which four distinct longitudinal lugs 34, 35, 36, 37 extend substantially orthogonally, uniformly distributed with respect to the axis of said wall:
  two diametrically opposed lugs 34, 35, each provided in the region of its free end with two lateral dogs such as 38, 39, adapted so as to be able to anchor in the needle-protecting end piece 3,
  two other diametrically opposed lugs 36, 37, each having, in the intermediate position of its length, an external projection such as 40 having an external surface provided with longitudinal notches such as 41 mating with the notches 16 of the cleavable section 8b. In addition, each projection 40 has a cylindrical rear portion 40a preceded by an inclined front portion 40b forming a slope.

It should be noted moreover, that as shown in FIG. 10, during moulding, the lugs 34–37 are produced in a substantially "open" position, namely inclined outwards with respect to the axis of the front wall 33.

Figure 2:
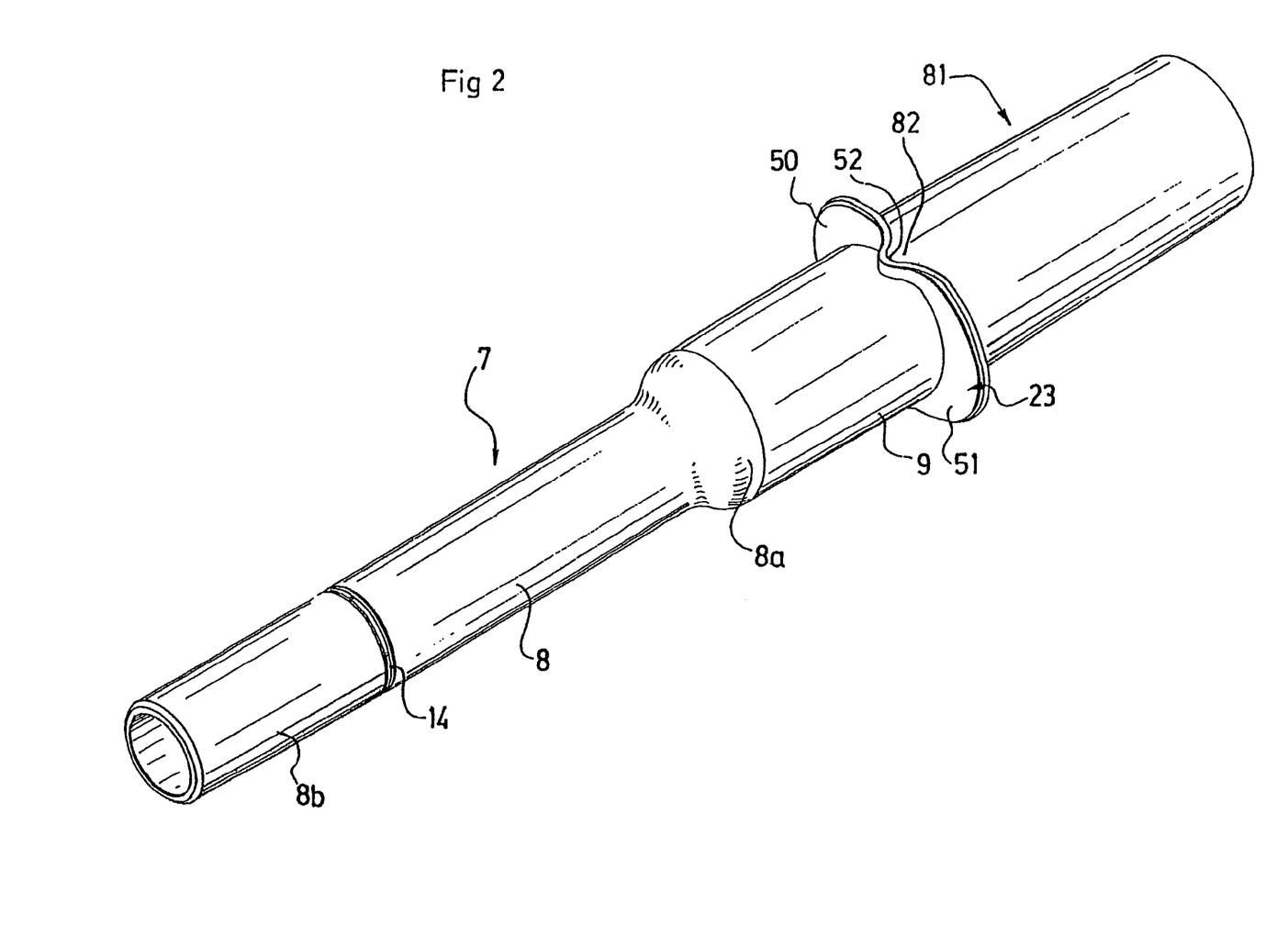
FIG. 2 is a perspective view of this injection device.

As shown in FIGS. 1 and 2, the injection device finally includes a protective cap 81 capable of covering the thrustor 6 and the rear ends of the piston rod 5 and of the protective case 7, so as to butt up against the collar 23.

This protective cap 81 comprises a lower edge having a profile complementary to that of the collar 23, and thus carrying two diametrically opposed lobes such as 82 with a convex shape mating with the concave shape of the undulations 52, 53 of said collar.

The specific shapes of the collar 23 and of the protective cap 81 make it possible first of all to obtain a tightening force ensuring that the protective cap is firmly held in place. In addition, they make it possible to withdraw the protective cap 81 easily by giving the latter a rotational movement which brings about an axial displacement of said protective cap on account of the matching concave and convex profiles of the indentations 52, 53 and lobes 82.

In addition, the protective cap 81 includes two diametrically opposed internal catches 83, 84 provided so that each of them is housed in an opening 80 of the protective case 7 when said protective cap is put in place. Such catches 83, 84 and openings 80 form a locking system which makes it possible, if not to eliminate safety seals, at least to reduce notably the resistance of the latter.

The steps for assembling this injection device are described below.

Figure 12:
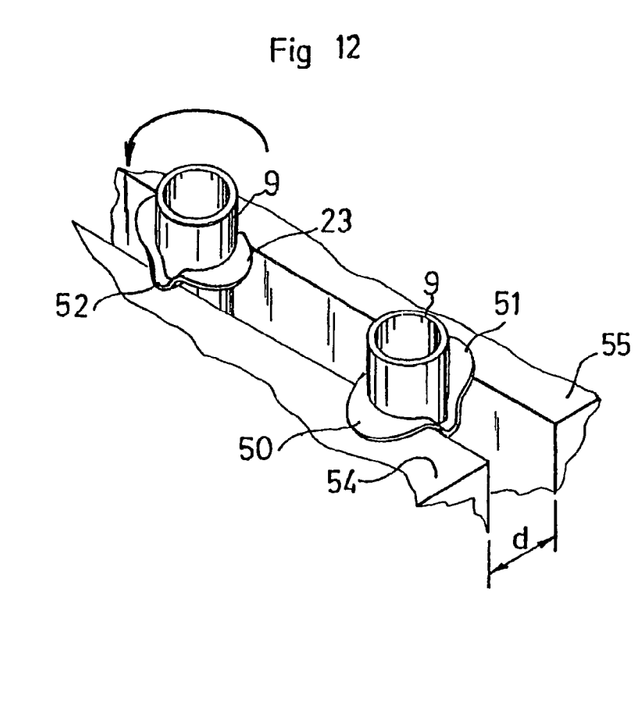
FIG. 12 is a diagrammatic perspective view of a transfer unit for the element of the protective case provided with finger rest components.

First of all, as shown in FIG. 12, the rear body 9 of the protective case 7 is guided between two parallel rails 54, 55, spaced by a distance d substantially greater than the diameter of said rear body.

During this guidance, and by virtue of the presence of the indentations 52, 53, this rear body 9 is led automatically to pivot on itself so as to be positioned in a stable position in which the supporting surfaces 50, 51 rest on the rails 54, 55.

At the end of this transfer, the rear bodies 9 are thus delivered with a substantially identical orientation in the region of a first assembly station adapted so that the locking ring 24 can be introduced inside said rear body.

To this end, this locking ring 24 is presented opposite the front surface of the rear body 9, until the ribs 27 are butted up against shoulder 20. It should be noted that this positioning is permitted by the elasticity of the tongues 21 and by the shape of the front surface 22b of the ribs 22 which forms a slope allowing these ribs to be crossed.

It should also be noted that once the locking ring 24 has been put in place, it is locked in rotation relative to the rear body 9 on account of the positioning of the ribs 27 in the grooves 19.

The rear body 9/locking ring 24 assembly that is pre-assembled in this way is then passed to a second assembly station.

Figure 13:
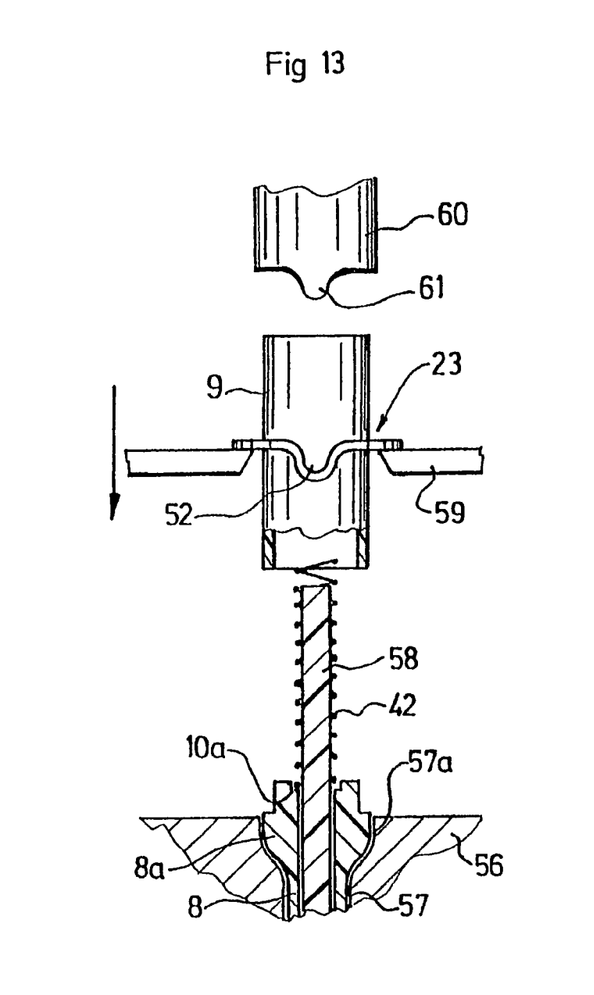
FIG. 13 is a diagrammatic view partially in section of a machine for assembling the two elements of the protective case.

This second assembly station, shown diagrammatically in FIG. 13, comprises first of all a frame 56 in which a bore 57 is provided emerging in the region of the upper surface of said frame through a recess 57a with an ovoid shape mating with that of the rear section 8a of the front body 8, enabling the position of said front body to be indexed.

This assembly station additionally includes a rod 58 adapted so as to extend inside the front body 8 positioned in the bore 57, and in the upper extension of said front body, said rod acting as a support for a spring 42 mounted around the latter so as to rest on the shoulder 10a of the ribs 10 of said front body.

This assembly station also includes holding devices 59 of any type known per se, adapted for positioning the rear body 9, previously indexed in rotation, in the axis of and above the rod 58, said holding devices being associated with means for movement in translation (not shown) capable of moving them along a vertical axis.

This assembly station finally includes a thrusting tool 60 with a tubular shape adapted so as to cover the rear section of the rear body 9, said tool having two lobes such as 61 adapted so that each is housed in an indentation 52, 53.

Such a tool 60 makes it possible first of all to correct any discrepancies in orientation and then to move the rear body 9 vertically without risk of any rotation of the latter, and finally to fit said rear body over the front body 8 by cooperation of the circlip 12 and the groove 18. Moreover, during this operation, the spring 42 becomes automatically compressed between the shoulders 10a of the ribs 10 and the shoulder 31. Finally, once assembled, the front body 8 and the rear body 9 are locked in relative rotation on account of the positioning of the catches 13 in the grooves 19.

At the end of these two operations, an entirely pre-assembled protective assembly is obtained, inside which the pre-filled syringe 1 may then be introduced as explained below.

Prior to this introduction, the end piece with dogs 32 is positioned on the needle-protecting end piece 3 of the syringe 1, at this stage lacking the piston rod 5. During this positioning, the lugs 34–37 of the end piece with dogs 32 are solely positioned around the needle-protecting end piece 3, without risk of forcing the latter and damaging the needle 2 and/or of destroying imperviousness.

The syringe 1, provided with the end piece with dogs 32, is then introduced into the rear body 9 of the protective case 7 until the collar 1b is brought so that it is locked between the ribs 29 and the shoulder 31. It should be noted that this introduction is permitted by the ability of the ribs 29 to deform and the shape of the slope of the rear surface 29a of these ribs 29 which allows the latter to be crossed by the collar 1b.

Moreover, during this introduction, the end piece with dogs 32 is led so as to be tightened onto the needle-protective end piece 3 during the passage of the projections 40 of the latter in the region of the slope 15 of the cleavable section 8b and of the neck 70, the passage being moreover facilitated by the shape of the slope of the front portion 40b of said projections.

It should be noted moreover that, as shown in FIG. 1, during this tightening, the dogs 38, 39 are anchored in the needle-protective end piece 3 downstream from the glass cone with which the front nose of conventional syringes 1 is traditionally provided, so as to ensure imperviousness. Accordingly, any risk of forcing the needle-protecting end piece 3 and thus of damaging the needle 2 and/or destroying imperviousness is eliminated.

Once this step has been carried out, it should be noted that the end piece with dogs 32 and the protective case 7 are locked in relative rotation on account of the cooperation of the respective notches 16, 41 of the latter. Moreover, on the one hand, the needle-protecting end piece 3 is locked in rotation with respect to the end piece with dogs 32 on account of the fact that the dogs 38, 39 are anchored in the latter and, on the other hand, this end piece with dogs 32, the protective case 7 and the locking ring 24 are also locked in relative rotation as explained above.

The last step finally consists of securing the piston rod 5 to the piston 4 in a conventional manner and then of putting the protective cap 81 in place. A ready-to-use injection device is thus obtained.

The invention claimed is:

1. An injection device comprising a syringe and an assembly for protecting said syringe, the assembly comprising a tubular protective case provided with finger rest components for gripping the injection device and for injecting a dose of a liquid, wherein the injection device has the finger rest components consist of a collar provided with an upper surface and a lower surface, the collar including two gripping portions with a symmetrical outline, said two gripping portions having lower supporting surfaces for the user's fingers thereon and between said supporting surfaces, two indexing portions with diametrically opposed symmetrical outlines, said two indexing portions including in the extension of the lower surface of said collar, a lower surface having a convex profile formed by two slopes symmetrical with respect to the longitudinal axis.

2. The injection device as claimed in claim 1, wherein each indexing portion of the collar has a lower surface having a curved profile with a convex rounded form.

3. The injection device as claimed in claim 1, wherein each indexing portion of the collar has the form of an undulation defining an indentation with a concave form.

4. The injection device as claimed in claim 3, further comprising a protective cap capable of covering the rear section of the protective case of the syringe so as to become butted up against the collar, wherein the protective cap has a peripheral wall provided with an end section comprising, for each indexing portion of the finger rest collar, a peripheral wall portion having a curved profile with a convex rounded form complementary to the upper surface of said indexing portion, adapted so as to fit into the latter.

5. The injection device as claimed in claim 4, wherein the protective cap includes means for locking that has at least one internal component for locking in translation, projecting with respect to the internal surface of the peripheral wall of the protective cap, the protective case of the syringe having a peripheral wall of which the outer surface has, in a position mating with each of said means for locking in translation, a recess capable of housing the latter.

6. The injection device as claimed in claim 5, wherein the means for locking the protective cap in translation consist of two diametrically opposed internal catches, each recess of the syringe body consisting of an opening capable of housing one of the catches.

7. The injection device as claimed in claim 2, wherein each indexing portion of the collar has the form of an undulation defining an indentation with a concave form.

8. The injection device as claimed in claim 1, wherein said liquid is a medicinal liquid.

* * * * *